(12) United States Patent
Greenwood et al.

(10) Patent No.: US 7,140,239 B2
(45) Date of Patent: Nov. 28, 2006

(54) SYSTEM AND TECHNIQUE FOR ULTRASONIC CHARACTERIZATION OF SETTLING SUSPENSIONS

(75) Inventors: Margaret S. Greenwood, Richland, WA (US); Paul D. Panetta, Richland, WA (US); Judith A. Bamberger, Richland, WA (US); Richard A. Pappas, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 107 days.

(21) Appl. No.: 10/391,070

(22) Filed: Mar. 18, 2003

(65) Prior Publication Data

US 2004/0182138 A1    Sep. 23, 2004

(51) Int. Cl.
  *G01N 33/34* (2006.01)
  *G01N 15/04* (2006.01)
(52) U.S. Cl. .................. 73/61.63; 73/53.03; 73/61.41; 73/61.62; 73/61.65; 73/61.66; 73/61.71; 73/61.75; 73/61.42
(58) Field of Classification Search ............... 73/53.03, 73/61.65, 61.75, 61.66, 61.41, 61.42, 61.62, 73/61.63, 61.71
  See application file for complete search history.

(56) References Cited

U.S. PATENT DOCUMENTS

| | | | |
|---|---|---|---|
| 3,666,419 A * | 5/1972 | Cahour et al. ................. 436/55 |
| 3,723,712 A * | 3/1973 | Komline et al. ............. 204/549 |
| 3,779,070 A | 12/1973 | Cushman et al. |
| 3,811,318 A * | 5/1974 | Killian ....................... 73/61.79 |
| 4,002,053 A * | 1/1977 | Hayakawa ................... 73/32 R |
| 4,114,427 A | 9/1978 | Iguchi et al. |
| 4,159,639 A | 7/1979 | Simms et al. |
| 4,344,321 A | 8/1982 | Haapamaki |
| 4,406,159 A | 9/1983 | Yanishevsky |
| 4,412,451 A | 11/1983 | Uusitalo et al. |
| 4,427,794 A * | 1/1984 | Lange et al. ................... 521/38 |
| 4,706,509 A | 11/1987 | Riebel |
| 4,708,011 A | 11/1987 | Rautakorpi et al. |
| 4,770,043 A | 9/1988 | Cobb et al. |
| 4,793,706 A * | 12/1988 | Csillag et al. ............... 356/335 |
| 4,895,019 A | 1/1990 | Lehmikangas et al. |
| 4,911,013 A | 3/1990 | Karras et al. |
| 4,963,229 A | 10/1990 | Lisnyansky et al. |

(Continued)

OTHER PUBLICATIONS

Mackaplow MB and Shaqfeh ESG. A numerical study of the sedimentation of fibre suspensions. J. Fluid Mech. (1998), vol. 376, pp. 149-182.

(Continued)

*Primary Examiner*—Hezron Williams
*Assistant Examiner*—Samir M. Shah
(74) *Attorney, Agent, or Firm*—Klarquist Sparkman, LLP

(57) ABSTRACT

A system for determining properties of settling suspensions includes a settling container, a mixer, and devices for ultrasonic interrogation transverse to the settling direction. A computer system controls operation of the mixer and the interrogation devices and records the response to the interrogating as a function of settling time, which is then used to determine suspension properties. Attenuation versus settling time for dilute suspensions, such as dilute wood pulp suspension, exhibits a peak at different settling times for suspensions having different properties, and the location of this peak is used as one mechanism for characterizing suspensions. Alternatively or in addition, a plurality of ultrasound receivers are arranged at different angles to a common transmitter to receive scattering responses at a variety of angles during particle settling. Angular differences in scattering as a function of settling time are also used to characterize the suspension.

12 Claims, 8 Drawing Sheets

U.S. PATENT DOCUMENTS

| | | | |
|---|---|---|---|
| 5,026,455 A | | 6/1991 | Lehtikoski et al. |
| 5,059,909 A | | 10/1991 | O'Brien |
| 5,076,890 A | | 12/1991 | Balembois |
| 5,121,629 A | | 6/1992 | Alba |
| 5,125,264 A | * | 6/1992 | Beuzard et al. ............ 73/61.75 |
| 5,359,906 A | | 11/1994 | Kanai |
| 5,454,912 A | | 10/1995 | Dougherty |
| 5,569,844 A | | 10/1996 | Sowerby |
| 5,616,831 A | * | 4/1997 | Ferland et al. ............. 73/61.63 |
| 5,635,632 A | * | 6/1997 | Fay et al. ................... 73/61.63 |
| 5,686,660 A | | 11/1997 | Lundberg |
| 5,789,676 A | * | 8/1998 | Fay et al. ................. 73/290 V |
| 5,939,622 A | * | 8/1999 | Fay et al. ................... 73/61.63 |
| 5,954,922 A | | 9/1999 | Ramarao |
| 6,012,324 A | | 1/2000 | Jakkula et al. |
| 6,018,989 A | | 2/2000 | Kubbillum |
| 6,044,702 A | | 4/2000 | Fay et al. |
| 6,044,703 A | | 4/2000 | Fay et al. |
| 6,105,424 A | * | 8/2000 | Fay et al. ................. 73/290 V |
| 6,119,510 A | | 9/2000 | Carasso et al. |
| 6,125,688 A | | 10/2000 | Matula |
| 6,205,848 B1 | | 3/2001 | Faber et al. |
| 6,234,023 B1 | | 5/2001 | Collins et al. |
| 7,010,979 B1 | * | 3/2006 | Scott ........................... 73/596 |
| 2003/0051535 A1 | * | 3/2003 | Coupland et al. .......... 73/64.53 |

OTHER PUBLICATIONS

Herzhaft B, Guazzelli E. Experimental study of the sedimentation of dilute and semi-dilute suspensions of fibres. J. Fluid Mech. (1999), vol. 384, pp. 133-158.

Povey, Malcolm J. W.. Ultrasonic Techniques for Fluids Characterization. (1997) Academic Press. pp. 47-90.

Allegra, JR and Hawley SA. Attenuation of Sound in Suspensions and Emulsions: Theory and Experiments. The Journal of the Acoustical Society of America. 51:(1972) pp. 1545-1563.

Atkinson, CM and Kytomaa, HK. Acoustic Wave Speed and Attenuation In Suspensions. 1992 Pergamon Press Ltd., pp. 577-592.

Derksen, JS and Kytomaa, HK. Acoustic Propererties of Solid-Liquid Mixtures in the Inertial Regime: Determination of the Added Mass Coefficient, FED-vol. 189, Liquid-Solid Flows ASME 1994, pp. 75-81.

Kytomaa, HK. Theory of sound propagation in suspensions: a guide to particle size and concentration characterization. Powder Technology 82 (1995) pp. 115-121.

* cited by examiner

SYSTEM AND TECHNIQUE FOR ULTRASONIC CHARACTERIZATION OF SETTLING SUSPENSIONS

GOVERNMENT RIGHTS

This invention was made with Government support under Contract Number DE-AC 0676RLO1830 awarded by the U.S. Department of Energy. The Government has certain rights in the invention.

FIELD OF THE INVENTION

The present invention relates generally to a method and apparatus for characterizing suspensions. More particularly, but not exclusively, the present invention relates to characterizing a suspension by performing ultrasonic interrogation during settling of solid particles. In one application, the invention is useful in characterizing complex suspensions and can be used, for example, in determining the properties of wood pulp fibers in a slurry of wood pulp and particle properties of solid-liquid suspensions.

BACKGROUND

Measurement of heterogeneous media in a continuous fluid phase, particularly solids in a fluid, is of commercial interest. Drilling fluids, slip casting, waste disposal, catalytic processes, paper manufacture, and many other commercial processes rely upon particles or solids in fluids. The development of practical and reliable methods for inspecting such fluid systems is of great interest because the properties of the fluid systems impact the quality of the resulting products and/or the energy efficiency of the process.

While there are several kinds of commercial equipment for particle size measurements based on the ultrasonic attenuation methods, these methods are limited by the mathematical inversion step for general cases in which the nature of the particle size distribution and physical properties of the particles are not known a priori. Furthermore, these methodologies do not completely account for the complexities of settling slurries.

The present invention is based, in part, on the fact that during settling a series of interfaces may develop and the fluid stratifies as a function of both particle size and shape. For instance, non-spherical particles orient preferentially during settling. The settling rate can depend upon the local solids loading, particle size distribution and solution (fluid medium) chemistry. In moving from the top to the bottom of a settling column, the particle sizes, shapes, composition, and concentrations can all be continually varying. The dynamics of suspension settling, controlled in part by the fluid medium properties, becomes a means to discriminate the particulate constituents in a suspension or slurry. By positioning ultrasonic interrogations at fixed locations along the settling column and monitoring the ultrasonic responses as a function of time provides a uniquely powerful means to characterize slurries and suspensions.

Moreover, while suspension characterization is important in a variety of situations, the accurate and reliable determination of slurry and suspension properties becomes increasingly important for systems where the properties are changing over time. For example, in paper manufacture, wood pulp is typically refined in a continuous operation where a slurry of wood pulp is processed to change the fiber characteristics, typically by passing the wood pulp through a pair of closely spaced rollers or rotating plates. The purpose of the refining is to change the characteristics of the fiber, which changes can involve splitting the outer and inner layers of the fibers, the splintering of smaller pieces of fiber or other debris and/or shortening of the length of some of the fibers. It is generally desirable to refine the pulp under conditions such that the fibers split without excessively shortening them or making significant amounts of debris. Accurate and reliable determination of pulp properties, such as the degree of refining and consistency of the pulp, can provide useful information for controlling this refining process or adjusting other aspects of the process to make a quality product from the wood pulp.

One common technique for determining the degree of refining of a wood pulp suspension is the freeness test, which is based on measuring the rate at which water drains from a pulp suspension through a wire mesh on which the fibers are retained in the form of a loose mat. Generally, the higher the degree of refining, the slower the water drains. One standard measure of freeness is termed the Canadian Standard Freeness (CSF).

Unfortunately, as well as being time consuming and labor intensive, the freeness test is an imperfect test that is not an accurate measure of the more important pulp qualities. For example, the freeness test is more strongly influenced by the presence and concentration of fines in the pulp than by the physical condition of the fibers. In addition, the refining process causes both fibrillation of the fibers and the rupture of the fibers' internal bonds such that the fibers become soft and swollen. The second effect, swollen fibers, results in improvement in the tensile strength properties of the paper. However, the freeness test is more a measure of fibrillation than of fiber swelling. Accordingly, it is desirable to characterize the degree of refining of wood pulp with a measure other than the freeness. See for example U.S. Pat. No. 4,159,639 to Simms et al. which is hereby incorporated by reference to the extent not inconsistent with the present disclosure.

Unfortunately, the ability to rapidly, reliably, and efficiently monitor suspension properties is limited. Accordingly, it is an object of the present invention to provide improved systems and techniques for determining properties of suspensions. While the present invention is broadly applicable to determining suspension properties for a variety of industrial suspensions in a variety of applications, in one form it is an object of the present invention to provide an apparatus and method to determine the properties of pulp fibers in a pulp suspension, as modified by the refining process, to facilitate prediction of the properties of the to-be-manufactured paper. In another form it is the object of the present invention to determine the particle properties of a settling solid-liquid suspension

SUMMARY OF THE INVENTION

In one embodiment the invention provides a novel technique for characterizing a suspension by substantially horizontally interrogating the suspension with ultrasound and receiving a response to the interrogating while allowing solids to settle in the suspension. The response to the interrogating as a function of time is then used to characterize the suspension.

One refinement includes interrogating with one of a pair of opposed ultrasound transducers located at a selected height in a settling column and receiving a response to the interrogating with a second one of the transducers at different times during the settling. In a further refinement, the solids are high aspect ratio particles, such as wood pulp fibers. In a still further refinement, a characteristic of the slurry is determined from the location of a peak in measured ultrasonic attenuation versus settling time data.

In another embodiment, a settling suspension is ultrasonically interrogated along an interrogation axis and a plurality of spaced receivers oriented at a plurality of different angles to the interrogation axis receive a response to the interrogating during particle settling. In one form, a multiplicity of receivers are configured in a substantially horizontal plane at a variety of different azimuthal positions with respect to a common ultrasonic transmitter. At the receivers, the amplitude, time-of-flight, and/or time-gated waveform can be measured for scattered, reflected and/or transmitted ultrasonic pulses over a range of frequencies and at different scattering angles during the particle settling. The received responses from one or more of the different receivers during the particle settling is then used to characterize the suspension. In one form the sample is characterized by comparing the response for one suspension to the response for a different suspension or to a library of responses. In an alternative or additional form, the responses are fit to empirical or theoretical models with multiple characteristics of the suspension substantially simultaneously determined via multivariate analysis. In one refinement, the received response includes at least two scattering responses received at different angles to the interrogation axis and the scattering responses at the different angles, when applied to a theoretical model, provides a measure of the particle size distribution of the settling particles. The angles can be both forward scatter or backward scatter angles, where the scattering angles are defined by the azimuthal orientation of a receiver with respect to a transmitter.

In one variation to the above embodiments, the settling characteristics of the suspension or slurry is controlled by modifying the solution chemistry with settling measurements performed under different suspension chemistries. For instance an adjusted solution pH can provide suspension constituent differentiation by promoting particle agglomeration. When the settling suspension is interrogated ultrasonically during particle settling under these various solution chemistries, variations in the settling properties based on solution chemsitry can be used to characterize the suspension.

Accordingly, it is an object of the invention to provide a technique for interrogating suspensions utilizing ultrasound.

It is another object to provide a system for characterizing suspensions.

It is a further object to provide a method whereby a suspension can be non-invasively characterized in an effective and efficient manner.

Further objects and advantages of this invention will be appreciated from a review of the complete disclosure and the appended claims.

DESCRIPTION OF PREFERRED EMBODIMENTS

Figure 1:
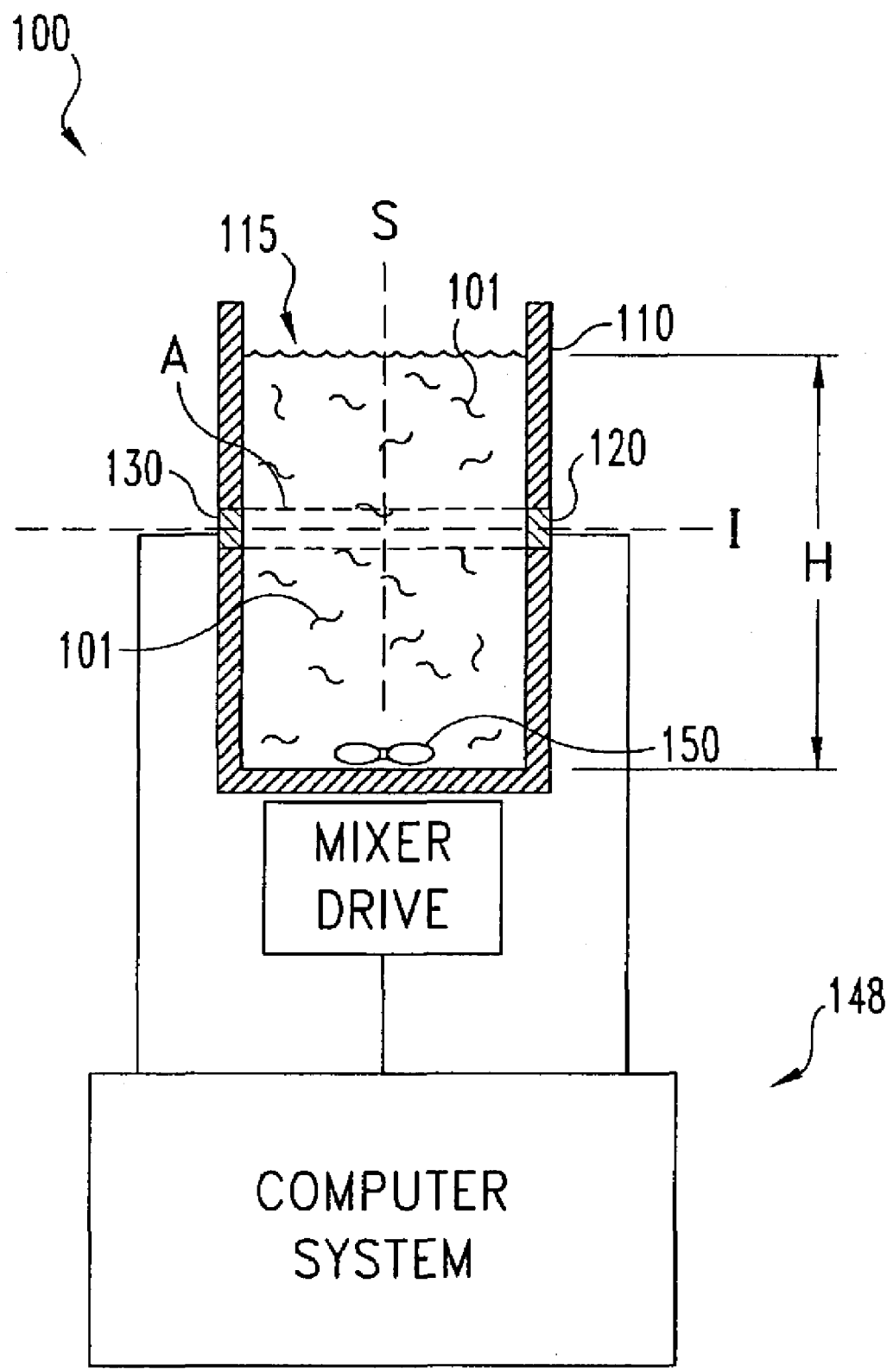
FIG. 1 is a schematic illustration of a system for characterizing a suspension with the particles of the suspension initially homogeneously dispersed throughout the suspension.

For the purposes of promoting an understanding of the principles of the invention reference will now be made to the embodiments illustrated in the drawings and specific language will be used to describe the same. It will nevertheless be understood that no limitation of the scope of the invention is thereby intended. Any alterations and further modifications in the illustrated embodiments, and any further applications of the principles of the invention as illustrated herein are contemplated as would normally occur to one skilled in the art to which the invention relates.

Certain embodiments of the present inventions relate to characterizing a suspension or slurry by performing ultrasonic interrogation during particle settling where the interrogation is performed in a direction transverse to the settling direction. The response to the interrogating is received as a function of settling time and typically exhibits substantial variation as the particles settle in the suspension. The variation in the response is a result of changes in the local concentration, microstructure, and/or morphology of the particles in the suspension during the settling process and the resulting changes in the propagation and/or scattering of ultrasound through the suspension. Both the settling behavior and the propagation and scattering of ultrasound are related to the characteristics of the suspensions, which for most industrial suspensions includes a particular size and/or shape distribution of particles. Accordingly, the time dependent response to the ultrasonic interrogating described herein provides unique information about the settling behavior of the suspension, which can then be correlated with or used as an indicator for certain characteristics of the suspension. Monitoring this time dependent response during particle settling has been found to provide a markedly effective means for characterizing a settling suspension such as the complex suspensions commonly encountered in a variety of industrial applications.

As used herein a suspension refers to solid particles suspended in a fluid, typically a liquid. A solid particle is any particle containing solid material and includes mixed phase particles, such as hollow particles. The liquid can be any liquid. The liquid selected is based either on the carrier required for the specific process or the inter-particle interactions that are desired to be expressed. Many industrial processes use water as the carrier. On the other hand, liquids of specific pH and viscosity can be used to promote or suppress particle aggregation or flocculation. Those of skill in the art will understand that by configuring the ultrasonic interrogation parameters, such as frequency, with the liquid properties, very specific suspension behaviors can be monitored by the techniques presented here.

Suspensions of solid particles in water are referred to as slurries. Settling of the particles refers to the net flux of particles in the settling direction and results in a significant change in the local particle concentration at a fixed fluid depth over time. Settling typically occurs as the result of a balance between the inter-particle interaction forces and the force of gravity as a result of density differences between the solid particles and the suspending fluid. In typical applications of the present invention, particles can be maintained in suspension by stirring the fluid or subjecting the fluid to turbulent flow, and particles can be allowed to settle by ceasing agitation or ceasing the flow. An external force or a change in suspension chemistry can also be utilized to cause, accelerate, or assist settling, for example through the use of centrifuge, pH change, or, in the case of magnetic particles, the application of a magnetic field.

The particles in a suspension can generally be any size or shape and can include entrained air or liquid material. In many applications the suspension will be complex, having particles of non-uniform size and shape. Typically complex suspensions include particles that are polydisperse and have a wide range of particle sizes and/or shapes. The different shapes include spherical, cylindrical, rod-like, fibrous, and/or irregularly shaped particles. In one aspect, the particles in the suspension include high aspect ratio particles, such as fibers. A high aspect ratio is a length to width ratio greater than about 5. Typical high aspect ratio particles have aspect ratios between about 5 and 30. Fibers or other high aspect ratio particles may be rigidly elongated or they may be flexible, assuming a variety of nonlinear shapes. In one particular application the suspension is a slurry of wood pulp, which is wood fibers suspended in water, as is utilized in the manufacturing of paper products.

The settling behavior of suspensions is influenced by a variety of factors, including the size and shape of the particles and the instantaneous microstructure of the suspension. Of course the instantaneous microstructure of the suspension itself changes over time as a consequence of particle settling. During settling, a series of interfaces may develop and the suspension may stratify as a function of particle size, particle shape, and particle density or volume fraction. For non-spherical particles or particles of irregular shape, the orientation of the particles adds another level of complexity to the settling behavior. For example fibrous or other high aspect ratio particles, may orient preferentially during settling and/or settle at a different rate than other particles in the suspension. The settling rate of any class of particles can depend upon the local solids loading, particle size and shape distribution, and suspension chemistry. Accordingly, at any fixed location in a settling column during particle settling, the distribution of particle sizes, shapes, composition, and concentrations can all be continually varying in a manner indicative of the suspension properties. In various embodiments, the present invention provides a mechanism to capture and quantify such variations and utilize them to characterize the suspension.

Figure 2:
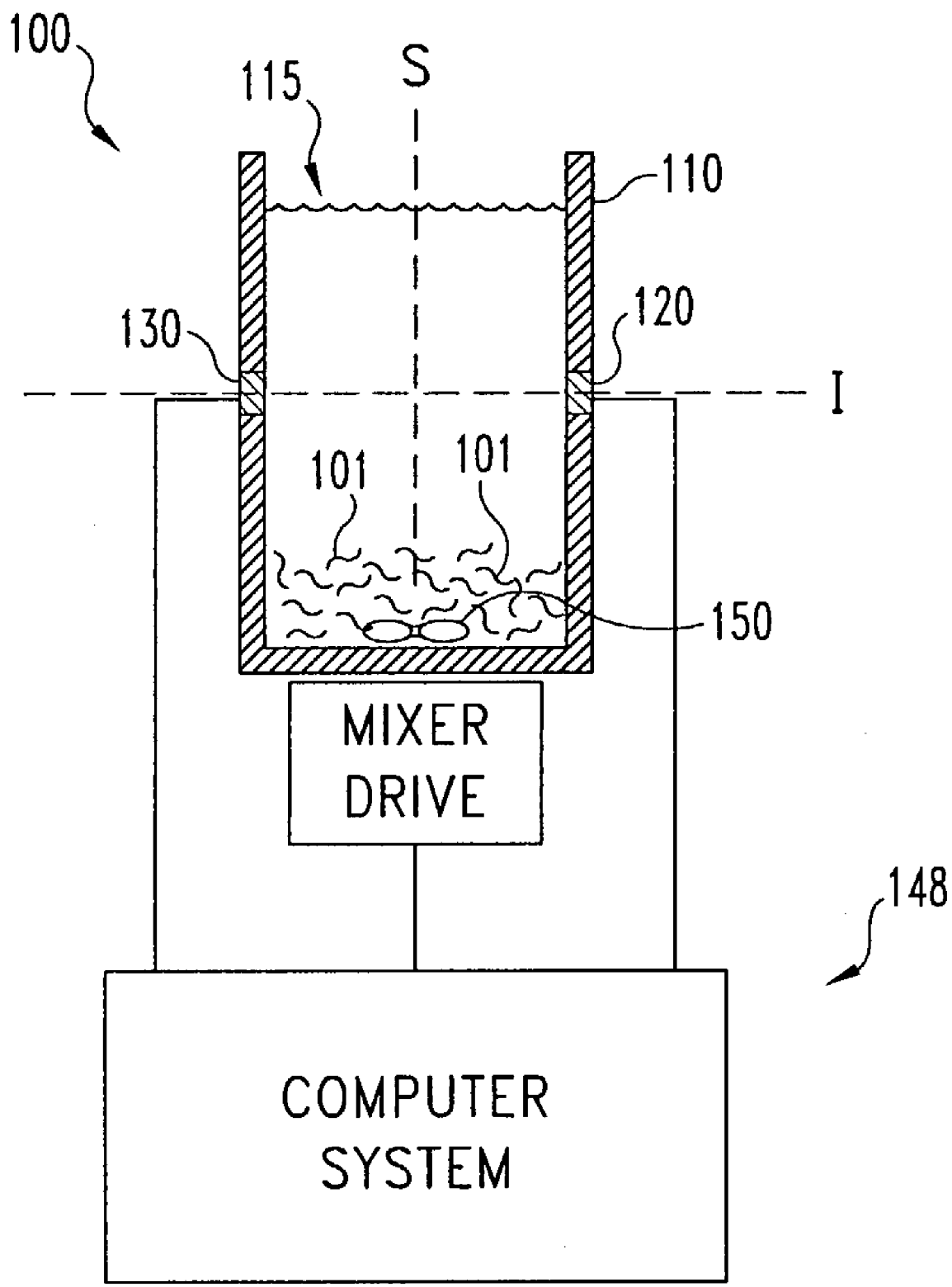
FIG. 2 is a schematic illustration of a the FIG. 1 system with the particles settled.

Referring to FIGS. 1 and 2, shown therein is a suspension characterization system 100 according to an aspect of the present invention. System 100 includes a settling container 110 for holding a sample volume of a suspension 115. The sample volume fills the container to a suspension height H. A pair of ultrasonic transducers 120, 130 are aligned along an interrogation axis I generally perpendicular to the settling axis S of the suspension containing a number of particles 101. For settling under the force of gravity, the settling axis S is a vertical axis because the denser particles 101 of the suspension will naturally tend toward the bottom of the container. The transducers 120, 130 are located below the top surface of the suspension along the suspension height H and are in acoustic communication with the suspension. The transducers 120, 130 are coupled to a computer system 148 and are operable to substantially horizontally interrogate the suspension with ultrasound and to receive a response to the interrogating to thereby ultrasonically determine a localized property of the suspension. As described more fully below, the entire suspension is then characterized by tracking localized changes during particle settling.

System 100 includes an agitation device or mixer 150 for agitating the suspension to maintain a homogeneous suspension of particles 101 until the onset of settling is desired. Settling commences when the mixer 150 is turned off. Useful mixers include a magnetic mixer or an impeller coupled to a shaft, a natural upward flow, or a pump to circulate fluid. Measurements made in a system with significant upward flow could increase the settling time of larger or more dense particles and could help to stratify the settling stream. An increased settling time may be advantageous when large or dense particles are suspended in a fluid of low viscosity. Care can be taken to operate the mixer to avoid the formation of gas bubbles in the suspension, as the presence of gas bubbles in the suspension can interfere with accurate ultrasonic measurements. Operation of the mixer is controlled by the computer system 148 which includes a clock to track the settling time. While there may be some residual fluid motion serving to keep the particles 101 in suspension for a brief period after the mixer 150 ceases agitation of the suspension (is turned off), for convenience, the settling time refers to the time after the mixer 150 is stopped.

Prior to performing the settling measurements to characterize the suspension, the suspension sample can be diluted to a consistency (or solids volume fraction) below the normal consistency of the suspension as it is being used. A useful volume fraction of solids for settling measurements is below about 10% by volume. For wood pulp suspensions, a useful consistency for settling measurements is between about 0.05% and 1% of wood pulp by weight, for example between 0.1% and 0.5%. The diluted suspension is provided in the settling container with the transducers located about midway along the suspension height H.

The suspension can be prediluted or provided into the container in more concentrated form and diluted to the appropriate consistency by the addition of liquid, such as degassed water, into the settling container 110. The mixer 150 can be operated to assure a homogenous suspension prior to settling. The container could also be operated at a pressure above atmospheric pressure to remove any effects of entrained air or other bubbles.

As described more fully below, the consistency of the suspension can be ultrasonically determined prior to the settling by performing attenuation measurements on the homogeneous suspension with the transducers 120, 130 and comparing the measured attenuation at a single frequency, or the attenuation spectrum obtained across a range of frequencies, to calibration values stored in the computer system 148. The relationship between attenuation and solids fraction is generally linear for dilute suspension.

The transducers can be piezoelectric transducers obtained from one of the many commercial vendor of ultrasonic transducers and equipment such as Xactex, Inc of Pasco, Wash. In one form, the transducers fully penetrate the walls of container 110 so as to have a transducer face in direct contact with the suspension. In other forms the transducers only partially penetrate the container walls or are mounted to the outside surface of the container 110 and acoustically communicate with the suspension through the walls of the container. With partial penetration or outside mounting, the transducers are clamp mounted or otherwise affixed to the container wall and an appropriate acoustic couplant is provided between the transducer face and the wall.

During the settling measurements, the transducers 120, 130 are positioned at a fixed location relative to the suspension height H and thus interrogate a fixed volume element A of the suspension 115 which is oriented as a generally horizontal cross section. The transducers 120, 130 are positioned approximately midway along the suspension height but could be positioned in other relative positions above or below the centerline. Optionally, the transducers 120, 130 can be positionable at a variety of heights, for example as a gimbaled fixture selectively slideable relative to the container 110, to find the optimum location for any particular application. In one form, the transducers are positioned at a sufficient height such that the majority of the particles in the suspension eventually settle at a level below the transducers 120, 130. Such a configuration is depicted in FIG. 2 wherein the particles have settled to the bottom of container 110 below the transducers 120, 130.

The size and configuration of the transducers determines the dimensions of the interrogated element A (see FIG. 1). The dimension of the interrogated element A along the settling axis S is less than the entire suspension height H, but it can be a significant fraction of the suspension height, for example 10–25% of the height H. The transmitting transducer 120 can be focused with the focal point at the vertical centerline of the container 110 or at some other point in the container. Unfocused or flat transducers, or those producing beams with a slight degree of divergence could also be used. The receive transducer 130 can also be flat, focused, or divergent. The transducers can be selected to have a reduced level of divergence in a direction parallel to the settling axis S to confine the ultrasonic interrogation to a section of the suspension 115 that is narrow along the settling axis S relative to the suspension height H. In one aspect, the transducers are elongated, for example rectangular, with their major dimension transverse to the settling axis S to have increased sensitivity in a narrow vertical slice of the suspension. In other variations, the transducers are symmetric or are elongated in another direction, for example elongated in the direction of the settling axis S.

Figure 3:
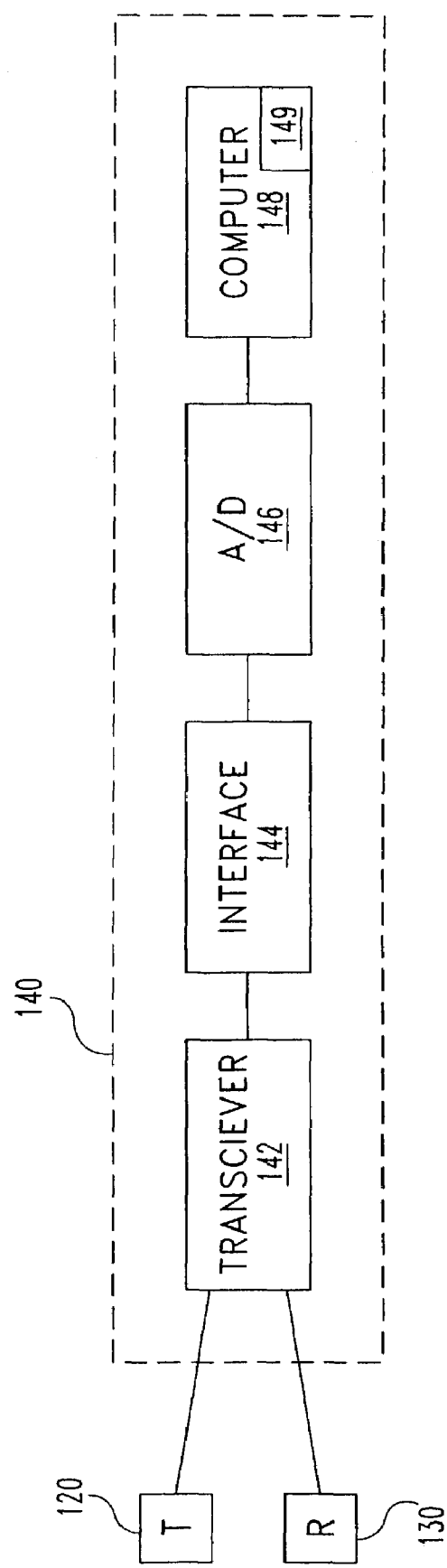
FIG. 3 is a block diagram of the ultrasound detection system used in the FIG. 1 system.

Turning now to FIG. 3, the transducers can be configured for operation in accordance with a broadband ultrasound detection system 140 under computer control. The detection system includes ultrasound transceiver 142, computer interface 144, analog-to-digital converter 146, and computer system 148. A voltage generator and pulser (in the transceiver 142) generates a sinusoidal stimulation of a specified number of cycles, for example 10, for amplification and transmission through the transmit transducer 120. The receive transducer 130 produces an output that, after appropriate amplification, is digitized and passed to a computer system 148. The electronics in the computer interface 144 generate the sampling clock used by the A/D converter 146. After A/D conversion, the data is stored on a disc drive 149 or other suitable fixed or removable memory device in the computer system 148.

The computer 148 includes programming instructions to processes the received response to determine its useful characteristics and to associate those characteristics with the settling time. Useful characteristics of the received response include without limitation, the amplitude of the received pulse, the phase or waveform of the received pulse, or the time of flight of the received pulse. The amplitude can be used to determine the attenuation of ultrasound through the suspension, and the time of flight can be used to determine an ultrasonic velocity (speed of sound) given a known distance between the transducers. The phase or waveform of the received pulse provides information about the beam spread and scattering that can also be correlated with suspension properties.

In one form, the attenuation of ultrasound as a function of settling time is used to characterize the suspension. Attenuation can be plotted as a function of settling time and the attenuation versus settling time curve used to characterize the suspension. The attenuation can be expressed as a relative attenuation of the solid particles by comparing to a reference attenuation value of the surrounding fluid. The attenuation is then plotted as a function of settling time by associating the relative attenuation with a settling time. An exemplary plot of attenuation versus settling time for four different suspension samples utilizing the apparatus of FIG. 1 is given in FIG. 7. As described in Example 1 below, this data corresponds to data obtained utilizing suspensions of wood pulp, but the system and technique is general and can be applied to other types of suspensions.

Figure 7:
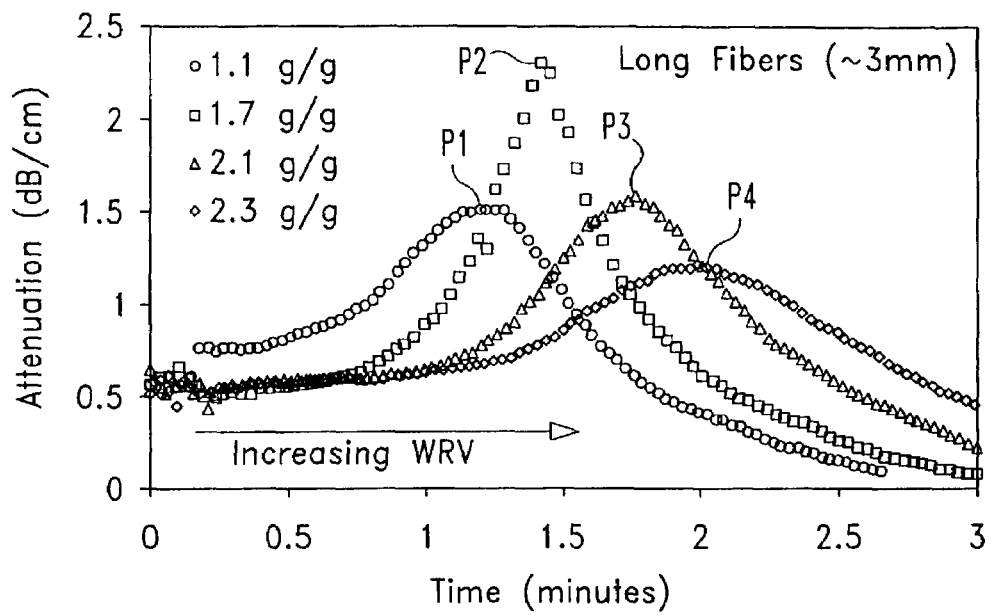
FIG. 7 is an exemplary plot of attenuation versus settling time for four settling suspensions having different characteristics. The depicted data correspond to settling of a slurry of wood pulp at constant consistency for four different water retention values for the wood pulp fibers. In each case, the fibers were approximately 3 mm in length.

For each of the different plots of FIG. 7, with increasing settling time, the attenuation shows an initial increases and then a steady decrease. This leads to a peak in each of the plots, designated as P1–P4 respectively. While not desiring to be bound by any theory or mechanism of operation, it is believed that the peak occurs because, when the stirrer is turned off, the particles of the suspension near the top of the container 110 start to fall into the volume between the faces of the transducers 120, 130. At the same time, the particles already in the area between the transducer faces start to fall toward the bottom of the container 110. These two rates—falling into and falling from the area between the two transducers 120, 130—are not equal throughout the settling process and depend, among other things, on the instantaneous local concentration of particles. Because the instantaneous local particle concentration changes, the two settling rates change leading to an initial increase and subsequent decrease in attenuation at a given location. At long settling times sufficiently after the peaks P1–P4, the attenuation tends towards zero as the concentration of particles between the transducers 120, 130 becomes substantially diminished, corresponding to particles settling below the transducers 120, 130 as depicted in FIG. 2.

As illustrated in FIG. 7, the shape of each of the plots of attenuation versus settling time for different suspensions is substantially different. These differences provide a mechanism to differentiate the suspensions based on the shape of their attenuation versus settling time plot. In one form, the computer 148 includes a library of attenuation plots and the suspension is characterized by matching a determined plot of an unknown sample to the library to find a best match. The characteristics of the unknown sample are then selected based on the characteristics of the library sample that matches best. A best match can be performed by fitting one or more curves to one or more portions of the plot and then selecting the best match based on the parameters of the curve fit. The bulk particle concentration or consistency of the suspension being measured can be determined, for example from a bulk attenuation measurement prior to the settling, to limit the library match to suspensions of similar bulk concentration.

In another form of processing, one or more values are calculated from the attenuation data and used to characterize the suspension. One such value that has been found to be useful in differentiating differences in suspensions is the peak time, which is the settling time when the attenuation data reaches its peak P1–P4. Changes in the peak time indicate changes in suspension properties. Accordingly, in one form of computer processing, the peak time is extracted from the attenuation versus time plot, and changes in peak time are monitored to determine qualitative changes in suspension properties. In another form, changes in the peak time are quantitatively correlated with changes in suspension properties, for example by developing a look up table or empirical relationship of suspension properties as a function of peak time. For example, it has been found that a logarithmic change in the peak time is generally proportional to a logarithmic change in the water retention value of wood pulp suspensions, with the proportionality factor empirically determined based on pulp type.

Alternatively or in addition, other aspects of the attenuation versus settling time curve can be utilized for correlation with suspension properties. For example, the initial increasing slope at early settling times is different for different suspensions and can serve as a value that can be correlated to suspension properties.

In still other alternatives or in addition, further information useful in characterizing the suspension can be extracted from the ultrasonic interrogation and the corresponding received ultrasonic response during particle settling. time For example, any of a variety of techniques may be used to estimate particle size distribution based on attenuation spectra. U.S. Pat. No. 5,121,629 to Alba, which is hereby incorporated by reference to the extent not inconsistent with the present disclosure, discusses one such ultrasonic method for determining size distribution and concentration of particle size in suspensions. In general, such a technique involves (1) directing ultrasonic waves through a suspension of particles wherein the ultrasonic waves exhibit multiple frequencies, (2) measuring attenuation at each frequency, (3) calculating an attenuation for each frequency from mathematical model(s), (4) comparing the measured attenuation spectrum with the calculated attenuation spectrum, and (5) selecting the particle size distribution and concentration that causes a match between the calculated and measured attenuation spectra. A useful mathematical model for determining the calculated attenuation spectrum is the Atkinson-Kytomaa model given in ACOUSTIC WAVE SPEED AND ATTENUATION IN SUSPENSIONS, CM Atkinson, HK Kytomaa, Pergammon Press Ltd. 1992, which is hereby incorporated by reference to the extent not inconsistent with the present disclosure. Determination of the particle size distribution can be done prior to settling as well as at discrete times during the settling.

By obtaining the particle size distribution at a variety of incremental settling times, the evolution of the particle size distribution in the interrogated area A between the transducers (see FIG. 1) can be tracked. The change in the particle size distribution as a function of settling time can be used to characterize the suspension. The bulk particle size distribution prior to settling can also be determined by taking an attenuation spectrum when the suspension is well mixed.

Figure 4:
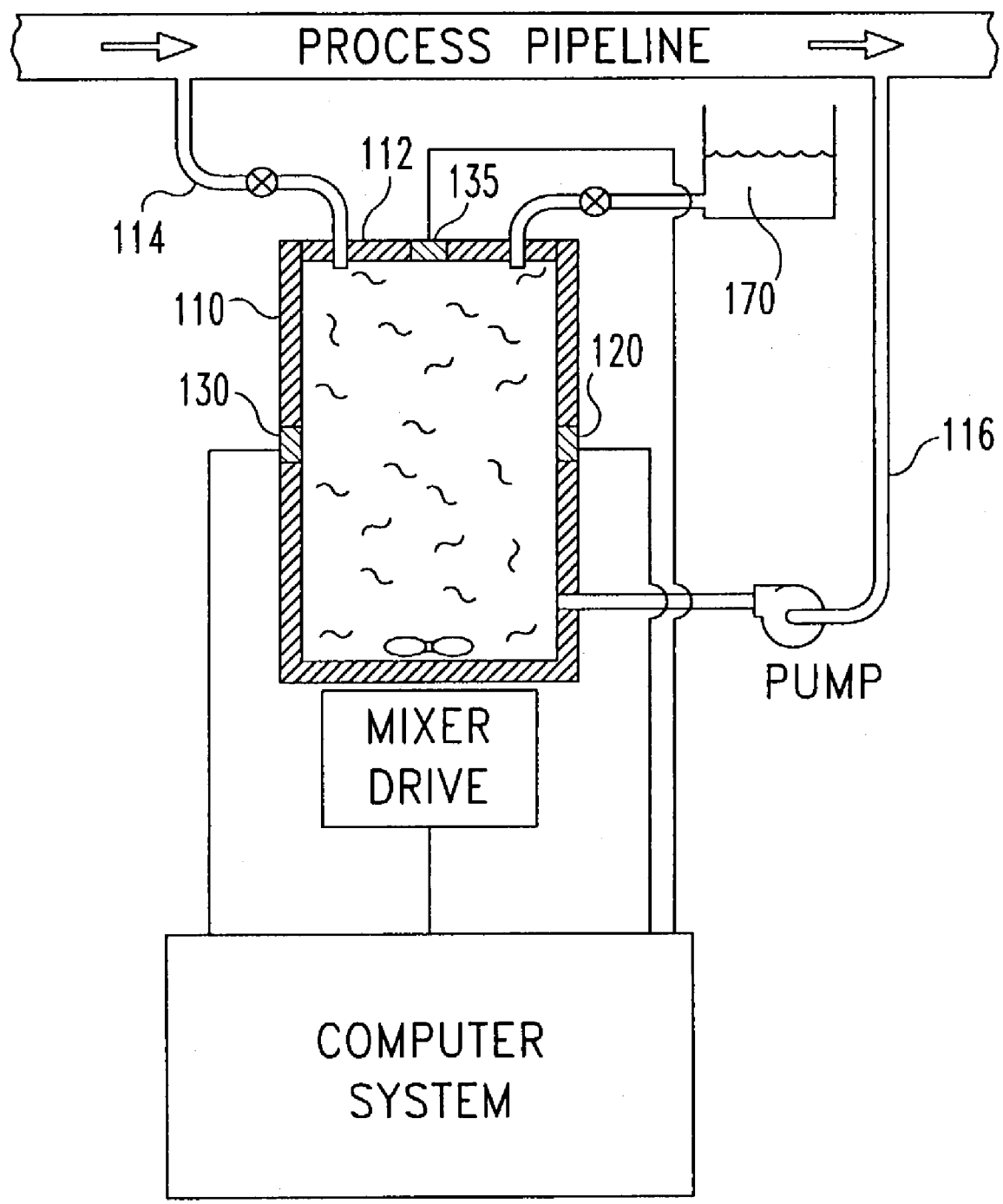
FIG. 4 is a schematic illustration of a variation of the FIG. 1 system implemented in a slip stream of a process pipeline and including a vertically mounted transducer.

The settling measurements of the present invention can be performed in a stand alone or laboratory setting, with samples to be interrogated manually provided to the settling container 110, or the device can be integrated for automated operation. One mechanism for automated operation is where the settling container 110 is implemented as a portion of a process stream. FIG. 4 illustrates a variation on the FIG. 1 device implemented in a slip stream to a process line. A valve on an inlet conduit 114 controls introduction of a suspension sample from the process pipeline and into the container 110, and a pump on the outlet line 116 returns the sample to the process line after testing. A dilution fluid reservoir 170 is connected to the container 110 such that a dilution fluid can be gravity fed, for example, to achieve the desired level of dilution prior to testing.

The container 110 in the FIG. 4 device is closed at the top 112 so that it can be pressurized as appropriate. Elevated pressures may be helpful to reproduce actual flow environments. Elevated pressures can also be used to reduce entrained air in the sample to increase sensitivity of the ultrasonic detection. An optional additional ultrasound transducer 135 is mounted in the top 112 of container 110 and coupled to the computer system. Transducer 135 operates in a vertical direction to transmit and/or receive ultrasound pulses. Transducer 135 can be used independently of, or in conjunction with, the horizontally-operated transducers 120, 130 to provide additional information on the suspension, such as by detecting and tracking settling particles and any interfaces that may develop during settling. Use of a vertically mounted transducer such as transducer 135 during particle settling is described in U.S. Pat. No. 6,105,424 to Fay et al. which is hereby incorporated by reference to the extent not inconsistent with the present disclosure.

Figure 5:
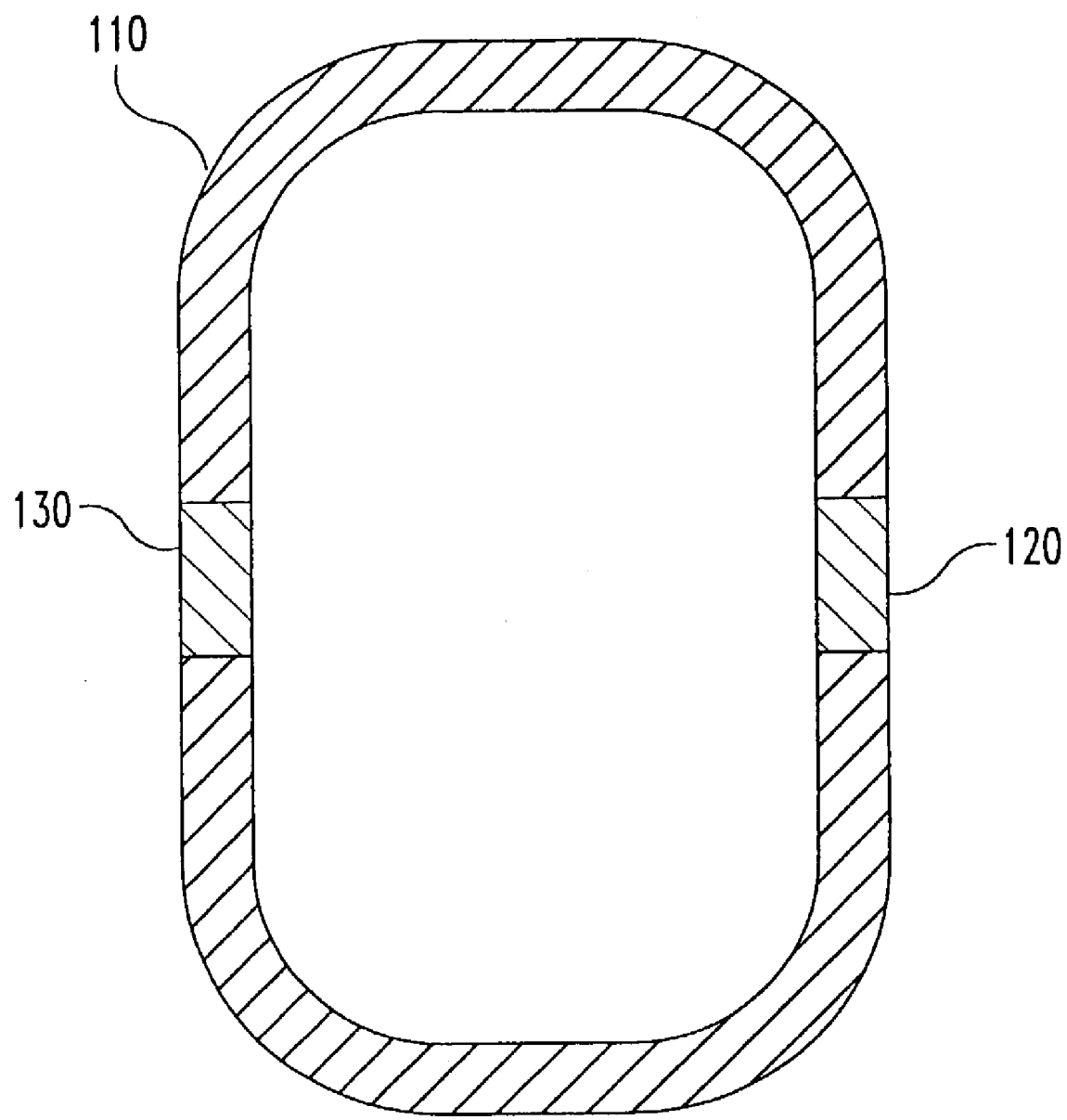
FIG. 5 is a cross sectional view of the settling container and transducers of FIG. 1 taken along the line of the interrogation axis I.

In other aspects of the invention, a plurality of transducers receive data during settling at a variety of angular positions. As depicted in the sectional view of FIG. 5, which is a view looking down the settling axis S of the FIG. 1 device, a single receive transducer 130 receives the response to the ultrasonic interrogation from the opposed transmitting transducer 120. As described more fully below, a plurality of receivers can also be utilized to each receive a response to the interrogating during particle settling.

Figure 6:
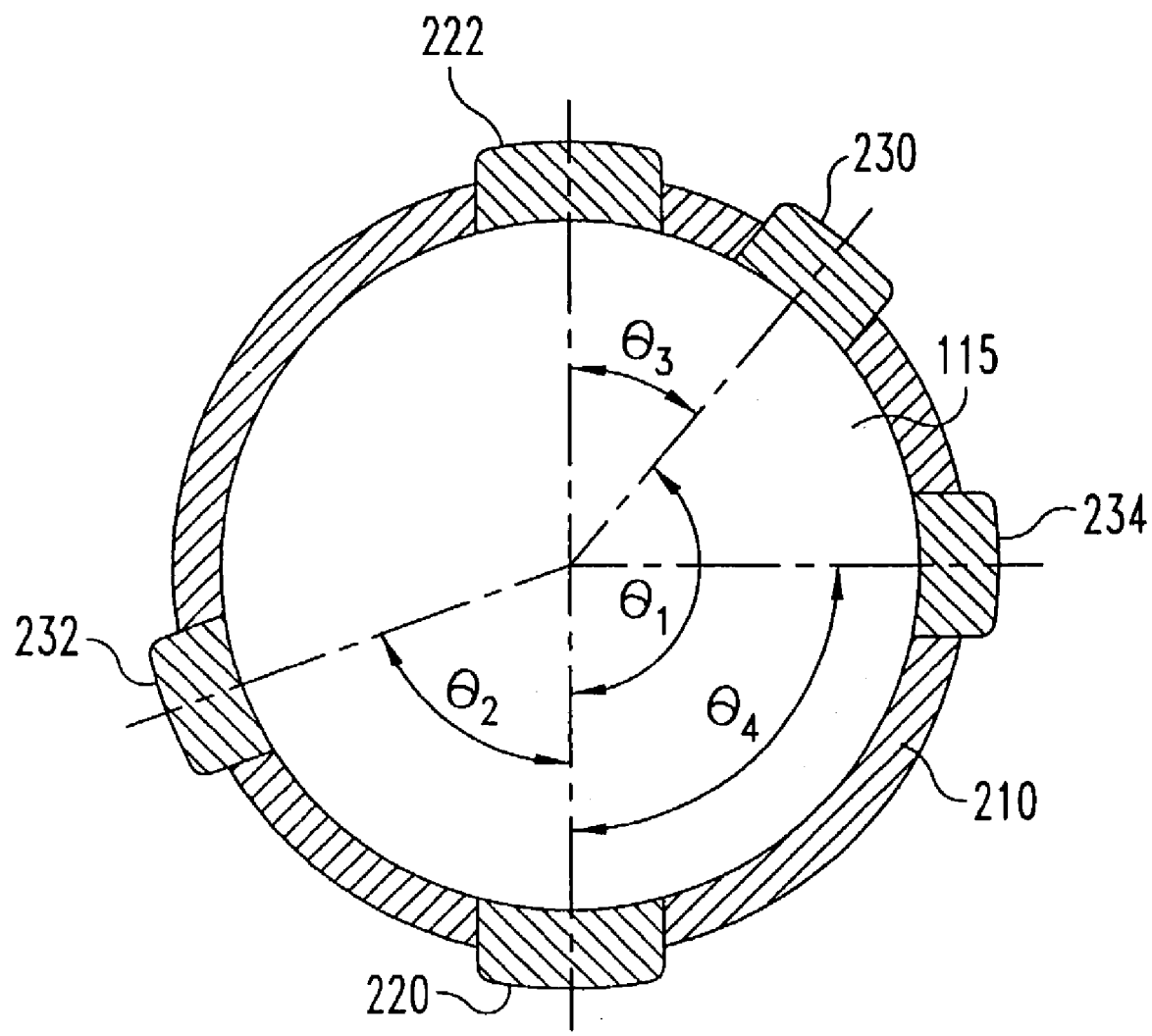
FIG. 6 is cross sectional view looking along the settling axis S of an alternative arrangement for the settling container and transducers for use in the FIG. 1 system wherein a multiplicity of transducers are arranged at varying azimuthal positions.

Turning now to FIG. 6, the cross section of a settling container 110 having a multiplicity of transducers 220, 222, 230 232, 234 each oriented in a common plane transverse to the settling axis is depicted. While it is to be understood that in various modes of operation, each of the transducers 220, 222, 230 232, 234 could operate as both a transmitter and a receiver, in one exemplary mode of operation transducers 220 operates as a transmitter. The remainder of the transducers are oriented at different azimuthal positions with respect to transducer 220 and receive the ultrasonic response. The azimuthal positions are defined by the angles between the axes of each of the transducers. Transducer 230 is oriented at an angle $\theta_1$ to transducer 220 where $\theta_1$ is an obtuse angle, for example about 150° C. Transducer 232 is oriented at an angle $\theta_2$ to transducer 220 where $\theta_2$ is an acute angle, for example about 60° C. Transducer 234 is oriented at an angle $\theta_4$ to transducer 220 where $\theta_4$ is approximately a right angle. Transducer 222 is diametrically opposed to transducer 220.

In operation, transducer 220 emits a tone burst signal at a preselected frequency into the settling suspension 115. The corresponding scattering response is received by transducers 230, 232, and 234. The through transmission signal is received by transducer 222 and the backscattered signal is received by the transmitting transducer 220. Each of these signals are digitized and passed to the computer through a multi channel analyzer. In a variation, transducer 220 transmits pulses of ultrasound at over a range of frequencies and a Fourier transform is performed to obtain the frequency response.

The time of flight is determined from the through transmission signal received at transducer 222 and the speed of sound is calculated from the known distance separating the transducers 220, 222. The time of flight/speed of sound is correlated with the settling time. Each of the received signals at transducers 230, 232, and 234 are time gated to select that portion of the scattering signal that most closely approximates the scattering from the center of the system. This time gate can be set based on the timing of the through transmission signal at transducer 222, which might change as the properties of the suspension change, in particular if the speed of sound through the suspension 115 changes appreciably during particle settling. The amplitude and waveform of each of received signal is also recorded and correlated with the settling time. One or more of these correlations with settling time are processed by the computer to be matched with library entries to find the best match with a predetermined suspension to determine the properties of the interrogated suspension. Alternatively, the received response can be correlated with mathematical models of settling and ultrasonic scattering, with the parameters of the suspension determined with multi-variate analysis.

As described above, transducer 222 is diametrically opposed to transducer 220. It is also oriented at an angle $\theta_3$ to transducer 230. As illustrated, angles $\theta_2$ and $\theta_3$ are different, and this configuration provides a mechanism to effectively increase the number of angular positions relative to a common transmitter without increasing the number of transducers. This is accomplished by switching between utilizing transducer 220 and transducer 222 as the transmitter. When transducer 220 is the transmitter, backscattering, or scattering detected at an acute angle, is detected at transducer 232, and forward scattering is detected at transducer 230. By contrast, when transducer 222 is utilized as the transmitter, backscattering is detected at transducer 230, which corresponds to a smaller angle. In either case, transducer 234 detects right angle scattering which should be independent of whether transducer 220 or 222 is used as the transmitter and can provide a reference for comparison between the two cases.

Having described systems and techniques operable to carryout the principles of the present invention, examples of the inventive systems and techniques are now presented.

EXAMPLES

Example 1

Settling measurements were performed on wood pulp with a system having a pair of horizontally opposed transducers according to FIG. 1. The measurements were carried out using one of two different sized oval-shaped vessels with circular transducers. A stirrer was placed in the vessel to keep the pulp suspended when desired. In the larger vessel the two horizontally opposed transducers had a diameter of 1.75 inches and were separated by 4 inches. The vessel had a depth of 5 inches and the transducers were vertically centered along the height. In the smaller vessel the two transducers had a diameter of 0.375 inches and were separated by 2 inches. The depth of the smaller vessel was 3.0 inches and the transducers were also vertically centered in the vessel. In both vessels the transducers were composed of films of polyvinyldifluoride (PVDF) and had a large bandwidth that permitted a single transducer to span a large frequency range. The frequency ranges for the transducers in were approximately 2.5 MHz to 15 MHz The transducers were connected to an electronic pulser-receiver in a data acquisition computer. The pulser-receiver contained a pulser to send a signal to the transmit transducer and a receiver to amplify the signal from the receive transducer. The pulser sent a sinusoidal pulse of about 10 cycles of the desired frequency to the send transducer. The resulting ultrasound pulse traveled through the suspension to the receive transducer which ouput a voltage proportional to the amplitude of the received ultrasound. The ultrasound pulse was attenuated as it traveled through the suspension such that the greater the attenuation through the suspension, the smaller the voltage recorded by the receiving transducer. The attenuation was expressed relative to a pristine water standard by comparing the signal obtained for any given suspension with the corresponding signal for water as follows:

$$\text{Attenuation} = -(20/D)\log_{10}(V_s/V_w), \quad (1)$$

Where $V_S$ is the voltage obtained when the vessel contains the suspension and $V_W$ when it contains water, with the voltages adjusted to account for the receiver gain. D is the distance between the two transducers. The attenuation has units of dB/cm. Software in the computer controlled the data acquisition system, stored the voltage $V_S$, and calculated the resulting attenuation. The voltages for water as a function of the frequency were stored in the computer code.

The system was configured to perform two types of measurements, measurement of attenuation spectra for a uniform suspension and measurement of attenuation as a function of settling time for a settling suspension. For the measurement of attenuation spectra, the mixer kept the pulp suspended while the attenuation was measured across a desired frequency range. The range of frequencies to be measured and the step change in frequency were input to the data acquisition code with measurement beginning with at the lowest frequency. After detecting the voltage on the receive transducer the frequency was sequentially incremented across the range. For the settling measurements, a mixer kept the pulp suspended initially and settling began when the mixer was turned off. During the settling the pulser operated at a single fixed value of the frequency to collect attenuation data as a function of settling time.

Settling Measurements

Four softwood pulp samples of different degrees of refining were obtained from Weyerhaeuser Inc. from their Prince Albert (PA), Canada mill. The pulp consisted of a mat of pulp fibers oriented in one direction and the Canadian Standard Freeness (CSF) and the water retention value (WRV) obtained in the conventional fashion for the four softwood samples are shown in Table 1. The CSF and WRV provide different measures of the degree of refining of the pulp. The sample with the largest value of CSF and the lowest WRV corresponds to unrefined pulp. CSF decreases with refining and WRV increases with refining.

TABLE I

Results of settling measurements for softwood pulp at 0.1 Wt % and 0.2 Wt %.
The relative peak time is defined as the peak time divided by the peak time
for the unrefined pulp.

| CSF (ml) | WRV (g/g) | Peak Time 0.1 Wt % Uncut Fibers (minutes) | Peak Time 0.2 Wt % Uncut Fibers (minutes) | Peak Time 0.1 Wt % Cut Fibers (minutes) | Relative peak time 0.1 Wt % Uncut | Relative peak time 0.2 Wt % Uncut | Relative peak time 0.1 Wt % Cut |
|---|---|---|---|---|---|---|---|
| 697 | 1.079 | 1.28 ± 0.18 | 2.48 ± 0.25 | 0.65 ± 0.05 | 1.0 | 1.0 | 1.0 |
| 652 | 1.745 | 1.52 ± 0.09 | 2.29 ± 0.04 | 0.74 ± 0.04 | 1.19 | 0.92 | 1.14 |
| 458 | 2.081 | 1.70 ± 0.08 | 3.03 ± 0.19 | 0.89 ± 0.04 | 1.33 | 1.22 | 1.37 |
| 293 | 2.298 | 2.00 ± 0.03 | 4.21 ± 0.09 | 1.12 ± 0.04 | 1.56 | 1.69 | 1.72 |

An accurate value of the weight percentage for each pulp sample was obtained by weighing a given sample before and after drying it in an oven. This weight percentage was then used to dilute the pulp to the selected weight percentage for the settling and attenuation spectral measurements. Settling data were obtained at an inspection frequency of 8 MHz and a suspension consistency of 0.1 Wt % and 0.2 Wt % utilizing the larger vessel filled to a level 1 inch below the top of the vessel. Exemplary data for 0.1 Wt % is present in FIG. 7.

Figure 8:
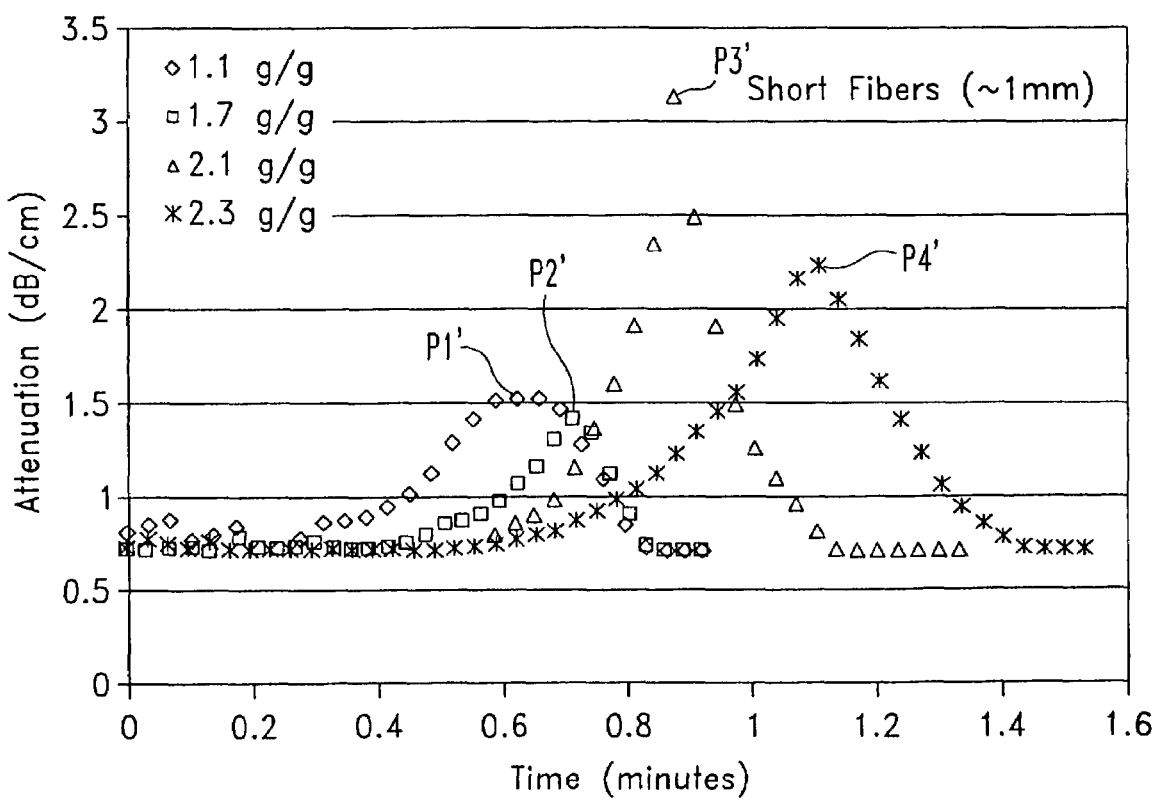
FIG. 8 is an exemplary plot of attenuation versus settling time for the suspensions of FIG. 7 wherein the fibers have been shortened to approximately 1 mm in length.

Since there are multiple measures of the degree of refining, one question relevant to the pulp manufacturing industry is which measure of degree of refining is being established. In other words, does a particular new measurement technique provide a measure of the water retention value or the Canadian standard freeness, or perhaps both? To answer this question a series of experiments were carried out after cutting the mat of fibers. As mentioned earlier, the wood pulp samples were provided as a mat of pulp fibers oriented in one direction. The mat was cut across the fibers in strips of about 1.5 mm. These cut fibers were then diluted to 0.1 Wt % and the settling measurements were repeated. Exemplary results of the settling for the shortened fibers is given in FIG. 8 using the same set up as described above for the uncut fibers.

The basic premise for the experiments with cut fibers is as follows: The Canadian Standard Freeness will be changed by cutting the fibers, but the water retention value, which is an intensive property of the pulp, will not be changed by cutting the fibers. Thus, if a measured parameter does not change with cutting, then that parameter is an indicator of the water retention value rather than the Canadian Standard Freeness.

Compared to the peak times for the corresponding uncut samples, the peak times are much shorter for the cut pulp samples. Accordingly, there is a qualitative correlation between peak times and fiber length, with increasing fiber length leading to increasing peak times. The peak time can thus be correlated with the Canadian Standard Freeness, with an increasing peak time indicating a decrease in the CSF. However, a relative peak time for a pulp sample, presented in Table 1 as the peak time for a particular refined pulp sample relative to the peak time for the unrefined pulp, is substantially unchanged for the various samples. Accordingly, this relative peak time can be said to be a measure of the water retention value of the pulp, because this relative value is substantially independent of fiber length.

Figure 9:
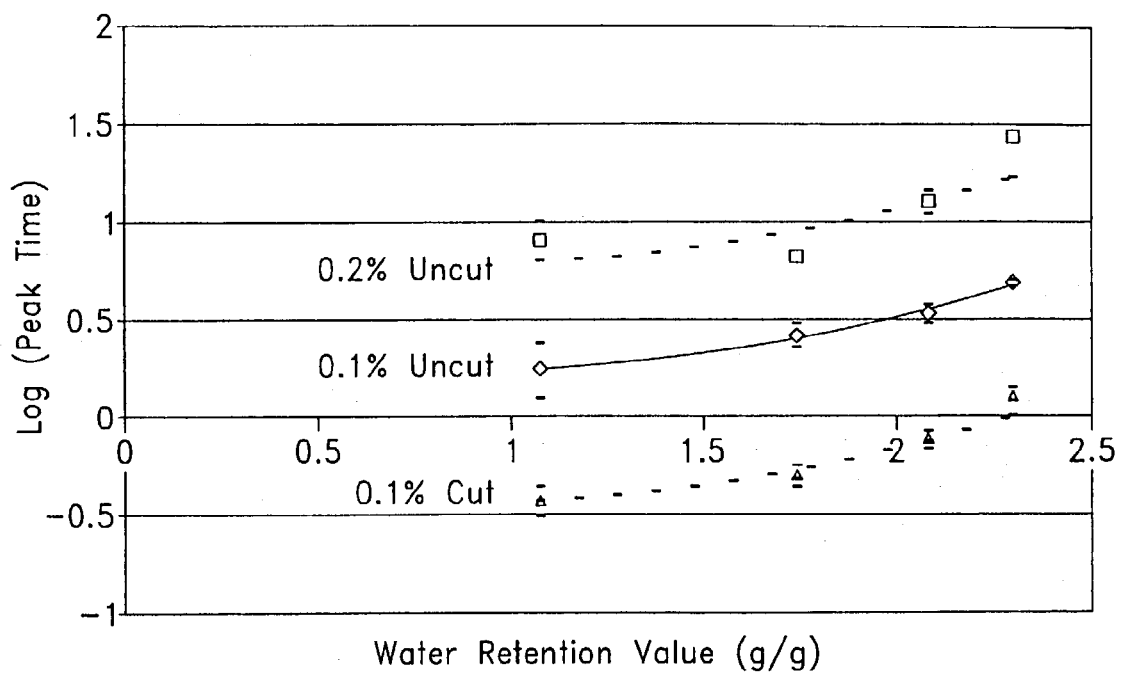
FIG. 9 is an exemplary plot of the log of the peak time versus the water retention value for pulp samples at two different consistencies for cut and uncut fibers at a single consistency.

FIG. 9 illustrates this concept of a normalized value of the peak time providing information that is insensitive to fibers length. FIG. 9 is an exemplary plot of the log of the peak time versus the WRV for cut and uncut pulp at the same consistency (0.1 Wt %) and for uncut pulp at a higher consistency (0.2 Wt %). At a given WRV, the absolute value of the peak time is a function of both the consistency and the fiber length (cut vs uncut). However, the shape of the curve of peak time versus WRV for a given consistency and fiber length (cut vs uncut) is constant, as shown by the consistency in the shape of the lines fit to the data.

Similar settling measurements on hardwood samples yield results qualitatively similar to those discussed above with respect to softwood pulp.

Figure 10:
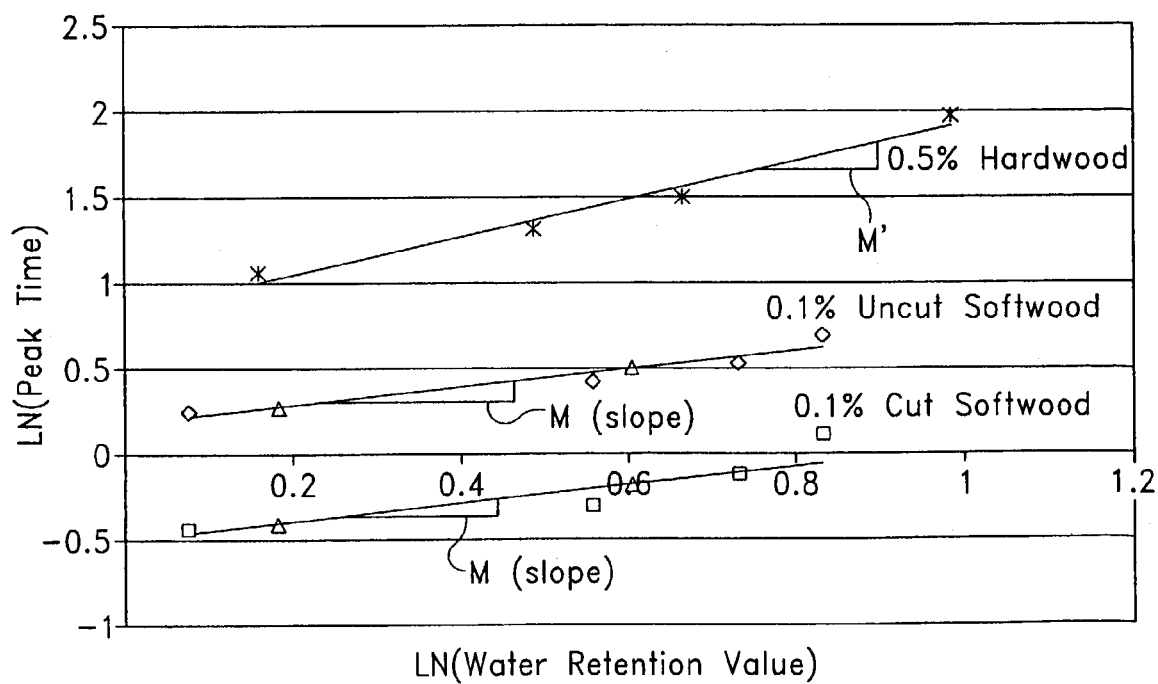
FIG. 10 is an exemplary plot of a logarithm of the peak time versus a logarithm of the water retention value for three different pulp samples with a straight line fit to each data set.

Turning now to FIG. 10, an exemplary plot of the log of the peak time versus the log of the WRV for three pulp series, cut and uncut 0.1 Wt % softwood and 0.5 Wt % hardwood pulp, are presented. A straight line is fit to each sample series and shows reasonable agreement with the data. The straight line fit for the different softwood samples (cut and uncut) is substantially identical in slope, providing an indication that the relative change in the log peak time with the log of the WRV is independent of fiber length. The linear fit to the hardwood samples also shows reasonable agreement with the data, though the value of the slope is slightly greater than the slope for the softwood samples. A mixture of hardwood and softwood pulp is expected to yield data conforming to a line with an intermediate slope.

An example of a method to monitor the refining of the pulp is to obtain the peak time for a pulp sample at a given consistency and then obtain the peak time for another pulp sample at the same consistency but at a later point in the refining process. An increase in the peak time for a given weight percentage indicates that the pulp is becoming more swollen, more refined, and thus more resistant to settling. A quantitative measure of the increase in refining, for use in monitoring or controlling the refining process, can be established as follows.

Define $T_1$ as the first measurement of the peak time, $T_2$ as the second one, and M as the slope of a straight line relating the natural log of peak time versus the natural log of WRV determined in advance for the type of pulp being refined. Useful quantitative information is $WRV_1$ and $WRV_2$, the WRV's of the different samples. The slope of the straight line is given by $$M = \frac{\ln T_2 - \ln T_1}{\ln WRV_2 - \ln WRV_1} = \frac{\ln\left(\frac{T_2}{T_1}\right)}{\ln\left(\frac{WRV_2}{WRV_1}\right)} \quad (2)$$

Solving Eq. 2 for the ratio $WRV_2/WRV_1$ we obtain the following:

$$\frac{WRT_2}{WRV_1} = \left(\frac{T_2}{T_1}\right)^{\frac{1}{M}} \quad (3)$$

Equation 3 provides a quantitative measure of the relative water retention value for the two samples based on the measured peak times and the slope. This value can be used to evaluate the effectiveness of the refiner settings and/or used to determine the actual value of the WRV based on a measurement or estimation of either $WRV_2$ or $WRV_1$. If additional information is known, then the relative water retention value can be determined more accurately. For example, suppose that the pulp has not been greatly refined yet. Then, the slope M in Eq. 3 can be given more precisely by the slope between the first two data points in FIG. 10.

In applications, the pulp may be a mixture of softwood and hardwood. Some settling measurements, combined with conventional measurements of the water retention value, could be used to provide calibration based on a particular pulp mixture. Precalibration for a range of pulp mixtures can also be employed, with a different slope M assigned to different pulp mixtures (percent hardwood vs. softwood). Alternatively, measurement of the relative peak times can provide a value for M if the WRV's are independently determined. M can then be used to estimate the percentage of hardwood and softwood in the mixture based on the precalibrated ranges of M for different mixtures.

Prior to performing the settling measurements, the consistency of the sample can be determined ultrasonically by examining the attenuation for a homogeneous suspension. The attenuation can be measured either at a fixed frequency or over a range of frequencies. Prior calibration establishes the relationship of attenuation with consistency. It has been found that frequencies between about 2 MHz and 7.5 MHz provide acceptable correlation for refined pulp with the relative attenuation being generally proportional to the consistency for the volume fractions of interest, below about 10% solids, in this frequency range.

In establishing the prior calibration for relating attenuation with consistency, increased accuracy can be achieved by only calibrating with pulp having undergone some degree of refining. The attenuation spectra for purely unrefined pulp has been found to vary to some extent from pulp having undergone varying (non-zero) degrees of refining. The variation of attenuation spectra for different (non-zero) degrees of refining and for different types of pulp is negligible, allowing a single calibration curve to relate attenuation to consistency for pulp having gone different (non-zero) degrees of refining.

Example 2

Settling measurements are performed on polydisperse suspensions with a settling container having an array of ultrasound transducers positioned at varying azimuthal positions about the settling axis as depicted in FIG. 6. As with Example 1 above, the suspension is initially agitated to maintain homogeneous suspension, and then agitation is stopped to commence settling.

During particle settling, transducer 220 transmits pulses of ultrasound at a preselected range of frequencies into the suspension and a scattering response is received by transducers 230, 232, and 234. The through transmission signal is received by transducer 222 and the backscattered signal is received by the transmitting transducer 220. Each of these signals are digitized and passed to a computer through a multi channel analyzer.

Each of the received signals at transducers 230, 232, and 234 are time gated to select that portion of the scattering signal that most closely approximates the scattering from the center of the system. The amplitude and waveform of each received signal is recorded and correlated with the settling time. The time of flight is determined from the through transmission signal received at transducer 222 and the speed of sound is calculated from the know distance separating the transducers 220 and 222. The time of flight is also correlated with the settling time.

For the polydisperse suspension, the particle size distribution in the volume interrogated by the transducers changes as a function of the particle settling. One reason for this is that different size particles tend to settle at different rates. Accordingly, because the relative scattering response at transducers 230, 232, and 234 will be a function of the particle size distribution, the scattering response at transducers 230, 232, and 234 will yield data sets that are different functions of the settling time. The differences among the entire set of scattering responses can be used to characterize the suspension.

For example, it is expected that for some suspensions, data peaks will occur at different times for each of the transducers 230, 232, 234. It is also expected that the relative spread between these peak times will change as the particle size distribution of the interrogated suspension changes, for example with a greater spread in peaks corresponding to a greater spread in particle size distribution. Accordingly, the relative spread in peaks for the transducers at different azimuthal positions provides a measure of the particle size distribution of the suspension.

While the invention has been illustrated and described in detail in the drawings and foregoing description, the same is to be considered as illustrative and not restrictive in character. Only preferred embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. Rather, the scope of this invention should be evaluated with reference to the claims appended hereto. Finally, all publications, patents, and patent applications cited in this specification are herein incorporated by reference as if each were specifically and individually indicated to be incorporated by reference and set forth in its entirety herein, including without limitation the following:

U.S. Pat. No. 4,159,639 to SIMMS, R. J. and MADSEN, B. K. titled "Apparatus and Method for Measuring the Degree of Refining of Pulp Fibers in the Preparation of Furnish for Paper Making," issued Jul. 3, 1979

GREENWOOD, M. S., MAI, J. L., GOOD, M. S., "Attenuation measurements of ultrasound in a kaolin-water slurry: A linear dependence upon frequency," J. Acoust. Soc. Am. 94, 908–916 (1993).

ALLEGRA, J. F. and HAWLEY, S. A., "Attenuation of Sound in Suspensions and Emulsions: Theory and Experiments," J. Acoust. Soc. Am. 51, 1545–1564 (1971).

HARKER, A. H. and TEMPLE, J. A. G., "Velocity and Attenuation of Ultrasound in Suspensions of Particles in Fluids," J. Phys. D: Appl. Phys. 21, 1576–1588 (1988).

What is claimed is:

1. A method for characterizing a suspension comprising:
   ultrasonically interrogating a selected location in a suspension of solid particles in a fluid in a settling container wherein the solid particles are initially substantially uniformly distributed through the volume of the suspension while allowing the solid particles to settle through the suspension for a settling time, wherein the interrogating occurs in an interrogation direction substantially non-parallel to the settling direction;
   receiving a response to the interrogating as the solid particles settle, wherein the received response provides an indication of a local property of the suspension at the selected location, the local property varying as a function of the settling time;
   forming a data set corresponding to the received response as a function of settling time;
   determining a characteristic of the suspension from the data set, including selecting a peak time corresponding to the settling time when the received response reaches a local extremum.

2. The method of claim 1 wherein the interrogating and receiving occur with at least one pair of opposed transducers and ultrasonic attenuation at the selected location in the suspension is determined as a function of the settling time.

3. The method of claim 1 wherein the determining further includes calculating a value corresponding to a relative peak time by comparing the selected peak time with a second peak time determined for a different sample.

4. The method of claim 3 further comprising selecting the second peak time from a plurality of peak times based on a solids concentration of the suspension determined prior to allowing the solids to settle through the suspension.

5. The method of claim 1 wherein the interrogating and the receiving occur with a pair of opposed transducers, the method further comprising determining the solid particle concentration of the suspension with the pair of opposed transducers prior to allowing the solid particles to settle through the suspension.

6. The method of claim 1 wherein the solid particles include particles having an aspect ratio greater than about 5.

7. The method of claim 1 wherein the solids concentration of the suspension is less than about 5% by weight.

8. The method of claim 1 wherein the suspension includes wood pulp.

9. The method of claim 1 further comprising modifying the chemistry of the suspension and repeating the interrogating and receiving for the modified suspension.

10. The method of claim 9 wherein modifying the chemistry includes modifying the pH of the suspension.

11. The method of claim 1 wherein the particle settling is at least partially induced by changing the suspension chemistry.

12. A method for characterizing a suspension comprising:
    providing a suspension of solid particles in a fluid in a settling container wherein the solid particles are initially substantially uniformly distributed through the volume of the suspension ultrasonically interrogating a selected location in the suspension while allowing the solid particles to settle through the fluid for a settling time, wherein the interrogating occurs in an interrogation direction substantially non-parallel to the settling direction;
    receiving a response to the interrogating, wherein the response is attenuated by the particles in the selected location, the response reaching a local extremum at a peak time, the peak time occurring when the number of particles falling into the selected location exceeds the number of particles falling out of the selected location.

* * * * *